United States Patent [19]

Lange

[11] 4,136,404

[45] Jan. 30, 1979

[54] ATHLETIC LEG BRACE APPARATUS

[76] Inventor: Robert B. Lange, 3732 Wonderland Hill Ave., Boulder, Colo. 80302

[21] Appl. No.: 777,510

[22] Filed: Mar. 14, 1977

[51] Int. Cl.$^2$ .......................................... A41D 13/00
[52] U.S. Cl. ........................................ 2/22; 128/80 R
[58] Field of Search ................. 2/22; 128/80 R, 80 C, 128/80 F, 80 H

[56] References Cited

U.S. PATENT DOCUMENTS

| | | | |
|---|---|---|---|
| 1,228,113 | 5/1917 | Hinson | 2/22 |
| 1,622,211 | 3/1927 | Sheehan | 2/22 |
| 2,144,641 | 1/1939 | Snyder | 2/22 |
| 2,587,166 | 2/1952 | Jovick | 128/80 C |
| 3,799,158 | 3/1974 | Gardner | 128/80 C |
| 3,826,251 | 7/1974 | Ross | 128/80 F |
| 3,827,431 | 8/1974 | Perorella | 128/80 F |
| 3,958,569 | 5/1976 | Vosburgh | 2/22 |

*Primary Examiner*—Werner H. Schroeder
*Assistant Examiner*—Doris L. Troutman
*Attorney, Agent, or Firm*—John J. Byrne

[57] ABSTRACT

An athletic leg brace apparatus of the type operable to be connected to the sides of a ski boot wherein the apparatus includes a first and second lower leg brace member and a first and second upper leg brace member. Each of the first upper and lower leg brace members and the second upper and lower leg brace members are connected by a ball joint hinge structure which preferably includes nested hemispherical shell members which are connected to respective portions of the leg brace members by a laterally extending axle positioned coaxially through the center of the hemispherical shells. A front portion of the first and second lower leg brace members and the first and second upper brace members are connected by a rigid semicylindrical member while the rear portion of the first and second lower brace members and the first and second upper leg brace members are interconnected by a flexible, adjustable connecting means. The lowermost portions of each of the first and second lower leg brace members are operable to be releasably connected to an upper lateral portion of a ski boot. The instant athletic leg brace apparatus permits an unemcumbered forward and rearward flexture of a skiers leg while concomitantly serving to restrict the lateral flexture of a skiers upper and lower leg portions and to transmit lateral forces on the skiers legs into the lateral portions of the skiers boot and ultimately the edges of the skiers skis for heightened performance characteristics.

13 Claims, 6 Drawing Figures

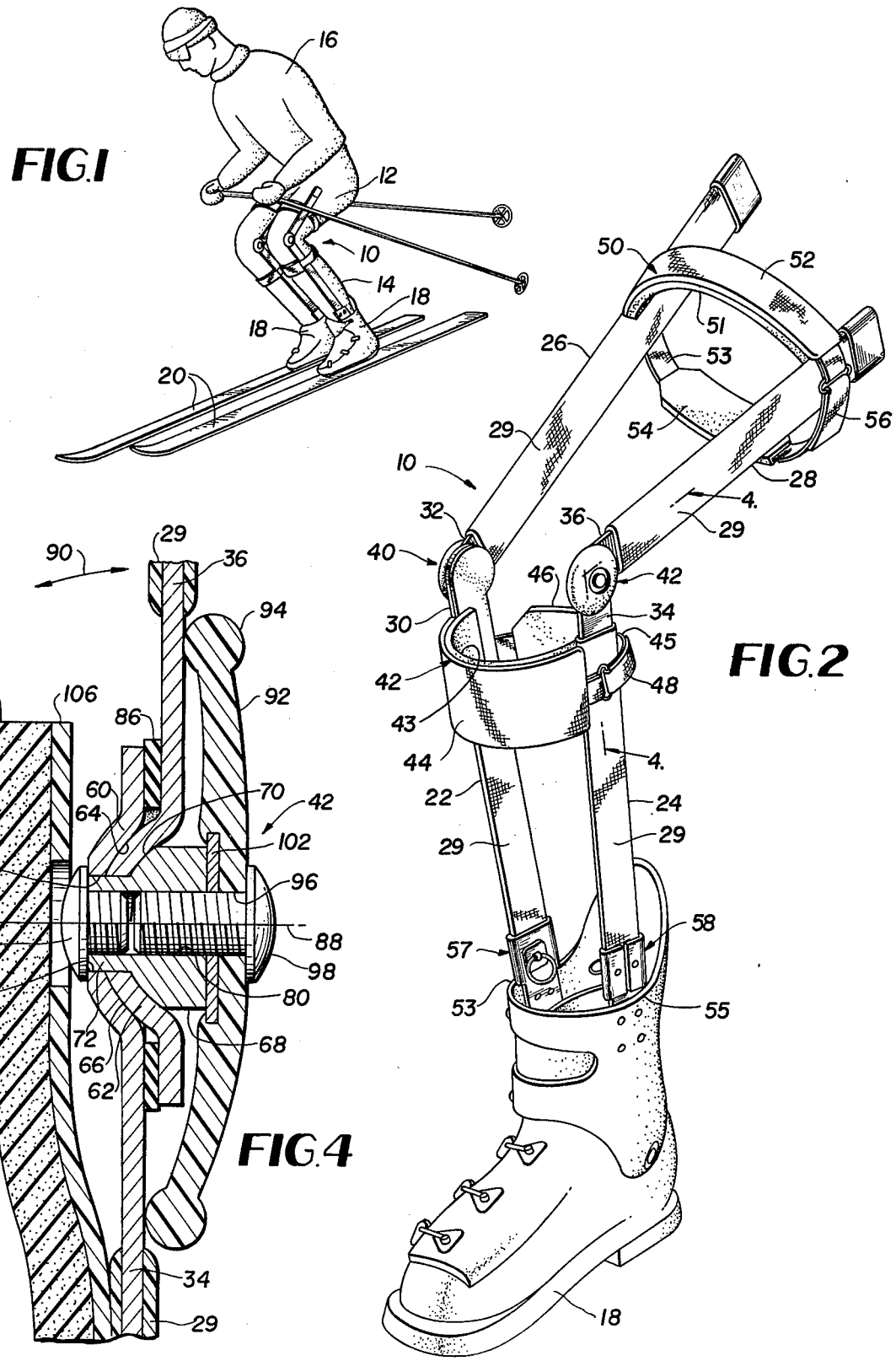

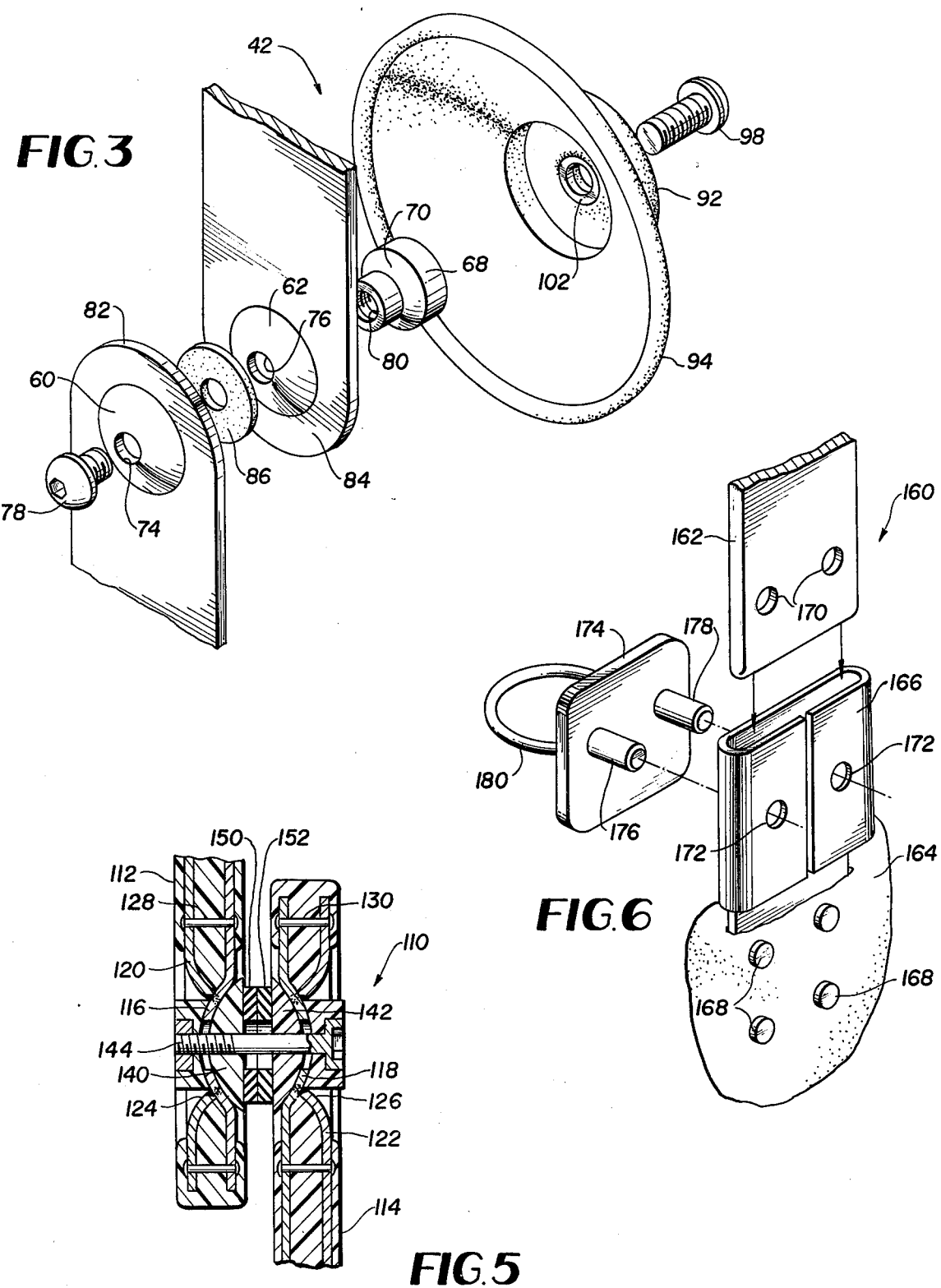

ATHLETIC LEG BRACE APPARATUS

BACKGROUND OF THE INVENTION

This invention relates to an athletic leg brace apparatus. More specifically this invention relates to an apparatus for enhancing the transmittal of lateral forces to the edge of a skiers skis while minimizing the possibility of damaging a skiers leg due to excessive lateral bending forces.

The sport of skiing encompasses inherent dangers to the leg bones of participants. This is not only true for the neophyte skier but also exists with respect to the average and even highly skilled alpine skiers.

While a neophyte skier is most likely to inadvertently lose control and fall in an awkward manner more skilled skiers occasionally push themselves beyond their limit, lose control and fall. Moreover, applicant has determined that even professional skiers in downhill events, and the like, place such bending strain on their legs during turns that the upper and lower leg bones actually tend to flex or laterally bend. Such an abnormal bone posture is extremely vulnerable in the event an unforseen bump or rut is encountered.

In addition to safety considerations a viable skiing apparatus must also provide adequate mobility and comfort to the skier. The mobility factor is important in relation to safety as mobility is a parameter which enables a skier to maintain an upright posture and control the "edge" of the skis.

In a similar vein it is believed that a skiers performance might be enhanced if it were possible to more effectively transmit lateral body forces into the edges of a skiers skis. In this regard some force is believed to be lost in bending a skiers legs and bones during cornering, etc.

Although broken legs and damaged knees due to excessive bending stresses created during a fall or with high speed skiing are well known in the ski world applicant is not aware of any technology which is designed to alleviate these vexing problems.

OBJECTS OF THE INVENTION

Accordingly it is general object of the invention to provide a novel apparatus which will obviate or minimize problems of the type previously described. It is a particular object of the invention to provide a novel athletic leg brace which will limit lateral flexing of a skiers upper and lower leg bones during skiing.

It is another object of the invention to provide a novel athletic leg brace which will permit a skier to enjoy normal forward and rearward flextural mobility.

It is yet another object of the invention to provide a novel athletic leg brace which will limit excessive lateral bending at a skiers knee while permitting a natural degree of lateral movement.

It is a further object of the invention to provide a novel athletic leg brace which will enhance the direction of force vectors generated by the skiers legs to the skis for heightened edging control and performance.

It is still further an object of the invention to provide a novel athletic leg brace which is adopted to fit a variety of skiers having different structural dimensions.

It is yet further an object of the invention to provide a novel athletic leg brace which is highly functional while concomitantly being streamlined and attractive enough to provide user acceptability.

BRIEF SUMMARY OF THE INVENTION

An athletic leg brace apparatus in accordance with a preferred embodiment of the invention which is intended to accomplish at least some of the foregoing objects includes a first and second lower leg brace and a first and second upper leg brace. The first and second lower leg braces are connected to the respective first and second upper leg braces by a ball joint hinge mechanism which preferably includes a pair of nested hemispherical shell members. A connecting pin extends transversely through the center of the hemispherical shell members and permits the leg brace members to be freely flexed in the forward and rearward position while at the same time permitting at least a degree of lateral flexure at the ball joint junction thereof.

A rigid cylindrical member extends between the first and second lower leg brace members and a second rigid cylindrical member extends between the first and second upper leg brace members. Flexible connecting members join the free ends of the first and second rigid cylindrical members and serve to securely mount the athletic leg brace upon the leg of a user.

The lowermost ends of the first and second lower leg brace members are operably received within a connecting unit attached to the lateral sides of the skier's boot and serve to releasably connect the subject athletic leg brace directly to the uppermost portion of the skiers boot and thus ultimately throught the boot to the edge of a skier's skis.

THE DRAWINGS

Other objects and advantages of the present invention will become apparent from the following detailed description taken in conjunction with the drawings wherein:

FIG. 1 is a pictorial illustration of a skier utilizing an athletic leg brace in accordance with a preferred embodiment of the invention positioned about the upper and lower portions of a skier's legs and connected directly to the uppermost portion of the skier's boots;

FIG. 2 is an axonometric view of an athletic leg brace connected directly to the top of a ski boot;

FIG. 3, note Sheet 2, is an expanded axonometric view of a leg brace ball joint knee connection in accordance with a preferred embodiment of the invention;

FIG. 4, note Sheet 1, is a detail cross-sectional view of a preferred ball joint connection assembly between the upper and lower leg brace members as previously depicted in FIG. 3;

FIG. 5 is a cross-sectional detailed view of an alternate preferred embodiment of the invention disclosing another ball joint construction assembly; and FIG. 6, note Sheet 2, is an expanded axonometric view of a connection assembly operable to releasably secure the subject athletic leg brace to a ski boot.

DETAILED DESCRIPTION

Referring now to the drawings wherein, like numerals indicate like parts, and particularly to FIG. 1 thereof the operative environment of the subject invention is disclosed. More particularly an athletic leg brace apparatus 10 is fitted onto the upper 12 and lower 14 portions of the legs of a skier 16. The athletic leg brace apparatus 10 is connected directly to the skier's boots 18 which in turn are bound to the skier's skis 20.

Referring now to FIG. 2, the subject athletic leg brace apparatus 10 is more clearly disclosed and includes a first lower leg brace 22 and a second lower leg brace 24. The brace apparatus 10 further includes a first upper leg brace 26 and a second upper leg brace 28. The leg braces 22, 24, 26 and 28 are designed to be mounted upon opposite sides of the upper and lower portions of the leg of a skier.

The leg brace members are each preferably fabricated from a lightweight metallic material and covered with a synthetic fabric sheathing 29 such as nylon or the like.

The uppermost portion 30 of the first lower leg brace 22 is connected to the lowermost portion 32 of the first upper leg brace 26 through the provision of a ball joint connecting assembly 40. In a similar manner, the uppermost portion 34 of the second lower leg brace 24 is fitted to the lowermost portion 36 of the second upper leg brace 28 by a ball joint connecting assembly 42. The ball joint connections 40 and 42 advantageously permit an unencumbered forward and rearward flex of a skier's knee and a limited degree of natural lateral motion in a manner which will be discussed more fully hereinafter.

The first and second lower leg brace members 22 and 24 are interconnected by a rigid cylindrical member 42 extending between front portions of the lower leg brace members. The rigid members 42 are covered with an internal padding 43 and a wrap of covering nylon fabric 44. A flexible binding 45 is connected to the free ends of the rigid cylindrical member 42 and serves to pass around the back of a skier's leg to secure the lowermost portion of the leg brace apparatus to the skier. The flexible binding 45 includes a bearing pad 46 and reversely layed end portions 48 which are provided with Velcrol release strips to adjustably secure the binding about the leg of a skier.

In a manner similar to the foregoing, the upper leg brace members 26 and 28 are interconnected with a rigid cylindrical connecting member 50 which may internally comprise overlapping arcuate halves which are adjustably mated together to permit width adjustment of the upper leg brace members. The back portion of the rigid brace 50 is provided with a coextensive padding 51 and a nylon covering 52. A flexible binding 53 extends between the free ends of the rigid brace 50 and includes an enlarged pad portion 54 and reversely layed end portions 56 which are provided with Velcrol release strips to secure the flexible retaining member 53 in an adjusted posture.

The lowermost portion of the lower leg brace members 22 and 24 are releasably connected to the lateral sides 53 and 55 of a ski boot 18 by releasable connecting assemblies 57 and 58 which will be discussed in detail more fully below.

Referring now particularly to FIGS. 3 and 4 of the drawings, there will be seen a detailed view of a ball joint assembly 42 in accordance with a preferred embodiment of the invention.

The assembly 42 includes a first hemispherical shell 60 stamped into an uppermost portion of a lower leg brace 34. A second hemispherical shell 62 is stamped into the lowermost portion of an upper edge brace 36 in a direction to nest with the shell 60. More specifically, the inner concave and spherical surface 64 of the shell 60 bears against the outer convex spherical surface 66 of the shell 62.

A retaining member 68 having a convex spherical surface 70 is fitted against the concave surface of shell 62 and includes an axial extension 72 which projects through axial apertures 74 and 76 fashioned through the shells 60 and 62 respectively. A retaining bolt 78 is threadly received within a bore 80 coaxially cut through the retaining member 68 to hold the ball joint bearing assembly together.

The peripheral edges 82 and 84 of the endmost portions of the leg brace members are spaced by a resilient washer 86 which is snugly retained between the brace members in a posture depicted in FIG. 4. This resilient washer 86 in cooperation with the spherical mating surfaces 64 and 66 permit the ball joint assembly 42 to be freely flexed about a central horizontal axis 88 of the retaining member 68 and further permits a degree of lateral flexibility in the directions of arrows 90 to accommodate natural lateral flexing of a knee joint of a skier.

The foregoing ball joint assembly 42 is protected by a resilient covering 92. The covering 92 includes a cup-shaped member 93 having an outer peripheral bearing bead 94 and an inner aperture 96. The aperture 96 is designed to be in coaxial alignment with the center of the retaining member 68. A threaded connector 98 extends through aperture 96 and is received within the threaded bore 80 coaxially extending through the retaining member 68. The connector 98 operates in cooperation with a bearing washer 102 to releasably connect the resilient covering 92 in a compressed or flattened condition about the ball joint assembly 42.

The resilient cover 92 operably surrounds and encompasses the structural bearing members and serves to prevent the accumulation of snow within the moving parts of the ball joint structure. The bias condition of the cup 93, as depicted in FIG. 4, induces the flexible cup to conform to and accommodate changes in pivotal position of the structural brace members as a skier's knee flexes.

The interior portion of the ball joint assembly 42 is covered by a protective cushion 104 which is carried by a backing member 106 mounted upon the lower leg brace member 24.

Referring now to FIG. 5, there will be seen an alternate preferred embodiment of a ball joint assembly 110 in accordance with the invention. A lowermost portion 112 of an upper leg brace and an uppermost portion 114 of a lower leg brace are each provided on the interior surface thereof with an outwardly projecting hemispherical stamping 116 and 118 respectively. The hemispherical stampings are each reinforced by a generally rectangular brace 120 and 122 which are fashioned with inwardly directed apertures 124 and 126. The apertures are united to exterior portions of the hemispherical shells by welding or the like and the braces are further connected to the brace members by rivots 128 and 130.

The hemispherical stampings 116 and 118 are positioned such that the concave surfaces thereof are mutually facing and serve to receive a first solid generally hemispherical bearing member 140 and a second solid generally hemispherical bearing member 142, respectively.

An axially positioned bolt 144 transversely extends through the bearing assembly 110 and serves as an axle to permit free pivoting of the upper and lower brace members.

The inner portions of the hemispherical bearing members 140 and 142 are separated by one or more disks 150 and 152 which serve to provide an axial space between the bearing members and thus permits at least a degree of lateral flexing of the brace members. The disk members 150 and 152 may be fashioned from a resilient material which will enhance the lateral flexing characteristics of the ball joint design.

Referring now to FIG. 6 there will be seen a releasable connecting assembly 160 designed to connect a lowermost portion 162 of a lower leg brace 24 to an upper lateral portion 164 of a skier's boot 18.

A generally hollow retaining collar 166 is mounted to the uppermost lateral portion 164 of a skier's boot through the provision of rivots 168 or the like. The lowermost portion 162 of the lower leg brace is preferably fashioned with a plurality of apertures 170 which are designed to coaxially align with apertures 172 fashioned within the retaining collar 166.

In order to releasably connect the lower portion of the leg brace to the upper lateral portion of the ski boot, a locking pad 174 is provided having a pair of retaining rods 176 and 178 designed to be snugly received within apertures 170 and 172.

A pull ring 180 is connected to the inward side of the locking member 174 so that a skier may facilely release the subject athletic brace apparatus from the upper portion of a ski boot 18.

In describing a skier's athletic leg brace apparatus in accordance with a preferred embodiment of the invention, those skilled in the art will appreciate several advantages expressly and/or inherently disclosed.

In brief summary, however, a particular advantage of the subject invention is the provision of an athletic leg brace apparatus which will limit lateral flexing of a skier's upper and lower leg bones while permitting free and unencumbered forward and rearward flexing of the skier's legs.

Another significant feature of the invention is the provision of ball joint connecting assemblies between the upper and lower brace members which permits a degree of lateral flexibility in the skier's knee while protecting the skier from excessive lateral bending forces.

Additionally, a significant aspect of the subject invention is the provision for translating force vectors from a skier's body more directly into his boots and ultimately the ski edges to permit enhanced edge control and performance.

The subject athletic brace apparatus is also designed to accommodate a variety of skier sizes and may be facilely connected and disconnected to a skier's legs and ski boots.

Yet another significant aspect of the invention is the provision of a flexible biased shield covering each of the ball joint assemblies which follows the contour of the brace members during flexing of a skier's knees without encumbering a skier's performance.

In describing the invention, reference has been made to preferred embodiments. Those skilled in the art, however, and familiar with the disclosure of the subject invention may recognize additions, deletions, modifications, substitutions and/or other changes which fall within the purview of the subject invention as defined in the following claims:

What is claimed is:

1. An athletic leg brace apparatus of the type operable to be connected to the sides of a ski boot comprising:
   first lower leg brace means for extending generally vertically along one lateral side of a skiers lower leg;
   second lower leg brace means for extending generally vertically along the other lateral side of a skiers lower leg;
   first upper leg brace means for extending generally vertically along one lateral side of a skiers upper leg;
   second upper leg brace means for extending generally vertically along the other lateral side of a skier's upper leg;
   first hinge means connected between an upper portion of said first lower leg brace means and a lower portion of said first upper leg brace means for permitting unencumbered forward and backward flexing of a skier's knee while substantially transmitting lateral forces through said first hinge means;
   first resilient means connected to said first hinge means for permitting lateral movement of said first hinge means;
   second hinge means connected between an upper portion of said second lower leg brace means and a lower portion of said second upper leg brace means for permitting unencumbered forward and backward flexing of a skiers knee while substantially transmitting lateral forces through said second hinge means;
   second resilient means connected to said second hinge means for permitting lateral movement of said second hinge means;
   first lateral means connected to said first and second lower leg brace means for securing said first and second lower leg brace means to the lower leg of a skier;
   second lateral means connected to said first and second upper leg brace means for securing said first and second upper leg brace means to the upper leg of a skier;
   first means at the lower portion of said first lower leg brace means for rigidly connecting said first lower leg brace means to one side of the boot of a skier; and
   second means at the lower portion of said second lower leg brace means for rigidly connecting said second lower leg brace means to the other side of the boot of a skier; wherein
   lateral flexing of a skiers upper and lower legs will be restricted and lateral forces of a skier's legs will be more effectively transmitted to a skiers boots and the edges of a skier's skis attached thereto.

2. An athletic leg brace apparatus as defined in claim 1 wherein said first and second hinge means each comprise:
   a ball joint bearing structure, and
   an axle pin transversely extending through the center of the ball joint and secured to the adjacent portions of the brace members for securing the ball joint and the upper portion of the lower brace and the lower portion of the upper brace to permit free forward and backward flexing of a skier's leg.

3. An athletic leg brace apparatus as defined in claim 2 wherein said ball joint bearing structure comprises:
   a first hemispherical shell member positioned upon one of said upper portion of said lower brace member and said lower portion of said upper brace member; and
   a second hemispherical shell member positioned upon the other of said upper portion of said lower brace member and said lower portion of said upper brace member, and wherein
   the outer convex surface of said first hemispherical shell member is nested within the inner concave surface of said second hemispherical shell member to form a ball joint bearing structure.

4. An athletic leg brace apparatus as defined in claim 3 wherein said first and second resilient means comprises:
resilient means positioned between said first hemispherical shell member and said second hemispherical shell member for providing clearance between said members and permitting a degree of lateral flexing through said ball joint bearing structure.

5. An athletic leg brace apparatus as defined in claim 4 wherein said resilient means positioned between said hemispherical shells comprises:
at least one resilient washer means for permitting a degree of lateral flexture through said ball joint bearing structure.

6. An athletic leg brace apparatus as defined in claim 2 and further comprising:
a resilient cup shaped member positioned over the outer portion of each of said first and second hinge means.

7. An athletic leg brace apparatus of the type operable to be connected to the sides of a ski boot comprising:
first lower leg brace means for extending generally vertically along one lateral side of a skiers lower leg;
second lower leg brace means for extending generally vertically along the other lateral side of a skiers lower leg;
first upper leg brace means for extending generally vertically along one lateral side of a skiers upper leg;
second upper leg brace means for extending generally vertically along the other lateral side of a skiers upper leg;
first hinge means connected between an upper portion of said first lower leg brace means and a lower portion of said first upper leg brace means for permitting unencumbered forward and backward flexing of a skiers knee while substantially transmitting lateral forces through said first hinge means;
second hinge means connected between an upper portion of said second lower leg brace means and a lower portion of said second upper leg brace means for permitting unencumbered forward and backward flexing of a skiers knee while substantially transmitting lateral forces through said second hinge means;
first lateral means connected to said first and second lower leg brace means for securing said first and second lower leg brace means to the lower leg of a skier;
second lateral means connected to said first and second upper leg brace means for securing said first and second upper leg brace means to the upper leg of a skier;
first means at the lower portion of said first lower leg brace means for connecting said first lower leg brace means to one side of the boot of a skier; and
second means at the lower portion of said second lower leg brace means for connecting said second lower leg brace means to the other side of the boot of a skier;
said first and second hinge means each including a ball joint bearing structure having,
a first hemispherical shell member positioned upon one of said upper portion of said lower brace member and said lower portion of said upper brace member,
a second hemispherical shell member positioned upon the other of said upper portion of said lower brace member and said lower portion of said upper brace member, and
ball means positioned between the concave surfaces of said first and second hemispherical shell members to form a ball joint bearing structure; and
an axle pin transversely extending through the center of the ball joint and secured to the adjacent portions of the brace members for securing the ball joint and the upper portion of the upper brace to permit free forward and backward flexing of a skiers leg; wherein
lateral flexing of a skiers upper and lower legs will be restricted and lateral forces of a skiers legs will be more effectively transmitted to a skiers boots and the edges of a skiers skis attached thereto.

8. An athletic leg brace apparatus as defined in claim 7 wherein said ball means comprises:
a first hemispherical member;
a second hemispherical member; and
at least one washer positioned between said first and second hemispherical members for permitting a degree of lateral flexture through said ball joint bearing structure.

9. An athletic leg brace apparatus of the type operable to be connected to the sides of a ski boot comprising:
first lower leg brace means for extending generally vertically along one lateral side of a skiers lower leg;
second lower leg brace means for extending generally vertically along the other lateral side of a skiers lower leg;
first upper leg brace means for extending generally vertically along one lateral side of a skiers upper leg;
second upper leg brace means for extending generally vertically along the other lateral side of a skiers upper leg;
first hinge means connected between an upper portion of said first lower leg brace means and a lower portion of said first upper leg brace means for permitting unencumbered forward and backward flexing of a skiers knee while substantially transmitting lateral forces through said first hinge means;
second hinge means connected between an upper portion of said second lower leg brace means and a lower portion of said second upper leg brace means for permitting unencumbered forward and backward flexing of a skiers knee while substantially transmitting lateral forces through said second hinge means;
said first and second hinge means each comprising,
a ball joint bearing structure; and
an axle pin transversely extending through the center of the ball joint and secured to the adjacent portions of the brace members for securing the ball joint and the upper portion of the lower brace and the lower portion of the upper brace to permit free forward and backward flexing of a skiers leg;
first lateral means connected to said first and second lower leg brace means for securing said first and second lower leg brace means to the lower leg of a skier;

second lateral means connected to said first and second upper leg brace means for securing said first and second upper leg brace means to the upper leg of a skier;

first means at the lower portion of said first lower leg brace means for connecting said first lower leg brace means to one side of the boot of a skier; and second means at the lower portion of said second lower leg brace means for connecting said second lower leg brace means to the other side of the boot of a skier; wherein lateral flexing of a skiers upper and lower legs will be restricted and lateral forces of a skiers legs will be more effectively transmitted to a skiers boots and the edges of a skiers skis attached thereto.

10. An athletic leg brace apparatus as defined in claim 9 wherein said second lateral means comprises:

a rigid semicylindrical shell member composed of a pair of laterally adjustable arcuate halves connected between a forward portion of said first and second upper leg brace means; and a flexible connector means connected between a rearward portion of said first and second upper leg brace means for securing said first and second upper leg brace means to the upper leg of a skier.

11. An athletic leg brace apparatus as defined in claim 10 wherein said ball joint bearing structure comprises:

a first hemispherical shell member positioned upon one of said upper portion of said lower brace member and said lower portion of said upper brace member; and a second hemispherical shell member positioned upon the other of said upper portion of said lower brace member and said lower portion of said upper brace member, and wherein the outer convex surface of said first hemispherical shell member is nested within the inner concave surface of said second hemispherical shell member to form a ball joint bearing structure.

12. An athletic leg brace apparatus as defined in claim 11 wherein said ball joint bearing structure further comprises:

at least one resilient washer means positioned between said first hemispherical shell member and said second hemispherical shell member for providing clearance between said members and permitting a degree of lateral flexing through said ball joint bearing structure.

13. An athletic leg brace apparatus of the type operable to be connected to the sides of a ski boot comprising:

first lower leg brace means for extending generally vertically along one lateral side of a skiers lower leg;

second lower leg brace means for extending generally vertically along the other lateral side of a skiers lower leg;

first upper leg brace means for extending generally vertically along one lateral side of a skiers upper leg;

second upper leg brace means for extending generally vertically along the other lateral side of a skiers upper leg;

first hinge means connected between an upper portion of said first lower leg brace means and a lower portion of said first upper leg brace means for permitting unencumbered forward and backward flexing of a skiers knee while substantially transmitting lateral forces through said first hinge means;

second hinge means connected between an upper portion of said second lower leg brace means and a lower portion of said second upper leg brace means for permitting unencumbered forward and backward flexing of a skiers knee while substantially transmitting lateral forces through said second hinge means;

first lateral means connected to said first and second lower leg brace means for securing said first and second lower leg brace means to the lower leg of a skier;

second lateral means connected to said first and second upper leg brace means for securing said first and second upper leg brace means to the upper leg of a skier;

first means at the lower portion of said first lower leg brace means for connecting said first lower leg brace means to one side of the boot of a skier; and second means at the lower portion of said second lower leg brace means for connecting said second lower leg brace means to the other side of the boot of a skier;

said first and second connecting means each comprising, a retaining member operable to be fixedly connected to an upper lateral portion of a ski boot and being dimensioned to receive the lowermost end of a lower leg brace means; and a pair of spaced retaining means for releasably securing said retaining member to said lowermost end of a lower leg brace means, wherein lateral flexing of a skiers upper and lower legs will be restricted and lateral forces of a skiers legs will be more effectively transmitted to a skiers boots and the edges of a skiers skis attached thereto.

* * * * *